United States Patent [19]

Chasar

[11] Patent Number: 4,584,146

[45] Date of Patent: Apr. 22, 1986

[54] TETRAKIS(2,6-DI-T-BUTYL-4-SUBSTITUTED PHENYL)4,4'-BISPHENYL DIPHOSPHITES

[75] Inventor: Dwight W. Chasar, Northfield, Ohio

[73] Assignee: The B. F. Goodrich Company, Akron, Ohio

[21] Appl. No.: 543,725

[22] Filed: Oct. 20, 1983

[51] Int. Cl.$^4$ .................... C07F 9/141; C08K 5/52
[52] U.S. Cl. .................... 558/156; 524/101; 558/95
[58] Field of Search ............... 260/930, 976; 524/101

[56] References Cited

U.S. PATENT DOCUMENTS

| | | | |
|---|---|---|---|
| 3,271,481 | 9/1966 | Kujawa et al. | 260/960 |
| 3,531,483 | 9/1970 | Gilles | 544/221 |
| 4,371,646 | 2/1983 | Minagawa et al. | 260/930 |
| 4,371,647 | 2/1983 | Minagawa et al. | 524/101 |
| 4,495,320 | 1/1985 | Chasar | 524/101 |

*Primary Examiner*—Anton H. Sutto
*Attorney, Agent, or Firm*—J. Hughes Powell; Alan A. Csontos; Nestor W. Shust

[57] ABSTRACT

Tetrakis(2,6-di-t-butyl-4-substituted phenyl)4,4'-substitutedbisphenyl diphosphites that are prepared from a hindered phenol and a non-hindered bisphenol have been found to be excellent stabilizers for organic materials subject to degradation, and form even more effective combinations with hydroxyphenylalkyleneyl isocyanurates, substantially and synergistically enhancing the stabilizing efficiency of the isocyanurate.

3 Claims, No Drawings

TETRAKIS(2,6-DI-T-BUTYL-4-SUBSTITUTED PHENYL)4,4'-BISPHENYL DIPHOSPHITES

BACKGROUND OF THE INVENTION

A number of hindered phenols and hindered bisphenols have been reacted with phosphorous trichloride in a variety of combinations in an effort to provide compounds that might have use as stabilizers for organic materials subject to degradation. It is generally considered necessary that only hindered phenols or hindered bisphenols be used to prepare the phosphorus condensation compounds in order to obtain the most efficient and effective stabilizing materials. If non-hindered phenols could be used to make such compounds, less expensive compounds that are more readily prepared could be realized.

SUMMARY OF THE INVENTION

Tetrakis(2,6-di-t-butyl-4-substituted phenyl) 4,4'-substitutedbisphenyl diphosphites that are prepared from a hindered phenol and a non-hindered bisphenol have been found to be excellent stabilizers for organic materials subject to degradation, and form even more effective combinations with hydroxyphenylalkyleneyl isocyanurates, substantially and synergistically enhancing the stabilizing efficiency of the isocyanurates.

DETAILED DESCRIPTION

The tetrakis(2,6-di-t-butyl-4-substituted phenyl)-4,4'-substitutedbisphenyl disphosphites of this invention have the general formula

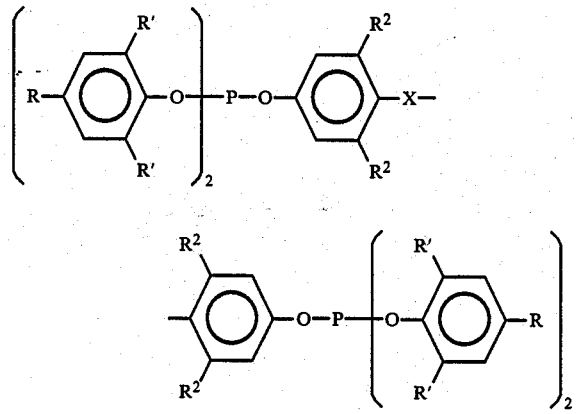

wherein R is an alkyl radical containing 1 to 9 carbon atoms, —OR$^3$ wherein R$^3$ is an alkyl radical containing 1 to 4 carbon atoms, —COOR$^4$ wherein R$^4$ is an alkyl radical containing 1 to 18 carbon atoms and

wherein R$^5$ is an alkyl radical containing 1 to 18 carbon atoms; R' is a t-alkyl radical containing 4 to 6 carbon atoms; R$^2$ are hydrogen or alkyl radicals containing 1 to 8 carbon atoms; and X is >CH$_2$, >CHCH$_3$, >CHCH$_2$CH$_3$, >CHCH$_2$CH$_2$CH$_3$, >C(CH$_3$)$_2$, —O—, —S—, >SO, or >SO$_2$. More preferably, R is an alkyl radical containing 1 to 4 carbon atoms, R$^4$ and R$^5$ contain 1 to 4 carbon atoms, R$^1$ is t-butyl or t-pentyl, R$^2$ is hydrogen, and X is —S—.

The tetrakis(2,6-di-t-butyl-4-substituted-phenyl)-4,4'-substitutedbisphenyl diphosphites of this invention are the reaction products of hindered phenols such as 4-substituted-2,6-t-alkylphenols, in the form of phosphorochloridite, with sodium phenolates of non-hindered bisphenols.

The 4-substituted-2,6-t-alkylphenyl phosphorochloridites are obtained, for example, from hindered alkylphenols having the formula

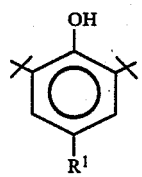

wherein + is a t-alkyl radical containing 4 to 6 carbon atoms, preferably t-butyl, R$^1$ is a primary, secondary, or tertiary alkyl radical contaiing 1 to 9 carbon atoms, —OR$^4$ wherein R$^4$ is an alkyl radical containing 1 to 4 carbon atoms, —COOR$^5$ wherein R$^5$ is an alkyl radical containing 1 to 18 carbon atoms, and

wherein R$^6$ is an alkyl radical containing 1 to 18 carbon atoms. Typical hindered phenols include 2,6-di-t-butyl-4-methylphenol, 2,6-di-t-butyl-4-propylphenol, 2,6-di-t-butyl-4-isopropylphenol, 2,6-di-t-butyl-4-amylphenol, 2,6-di-t-butyl-4-isoamylphenol, 2,6-di-t-butyl-4-heptylphenol, 2,6-di-t-butyl-4-octylphenol, 2,6-di-t-butyl-4-isooctylphenol, 2,6-di-t-butyl-4-methoxyphenol, 2,6-di-t-butyl-4-ethoxyphenol, 2,6-di-t-butyl-4-carbomethoxyphenol, 2,6-di-t-butyl-4-(2-carboethoxyethyl)phenol, 2,4,6-tri-t-butylphenol, 2,6-di-t-butyl-4-carbohexadecyloxyphenol, 2,6-di-t-butyl-4-(2-carbooctyldecyloxyethyl)phenol, 2,6-di-t-butyl-4-nonylphenol, and the like.

The phosphorochloridites are readily prepared by reacting 1 mol of PCl$_3$ with 2 or more moles of 4-substituted-2,6-di-t-butylphenol in an oganic solvent in the presence of the trialkylamine catalyst in accordance with the procedures of U.S. Pat. No. 3,271,481.

The bisphenols have the general formula

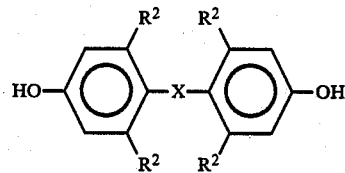

wherein the R$^2$'s are hydrogen or alkyl radicals containing 1 to 8 carbon atoms, and X is >CH$_2$, >CHCH$_3$, >CHCH$_2$CH$_3$, >CHCH$_2$CH$_2$CH$_3$, >C(CH$_3$)$_2$, —O—, —S—, >SO, or SO$_2$.

Typical bisphenols include 4,4'-methylene bisphenols, 4,4'-ethylidene bisphenols, 4,4'-propylidene bisphenols, 4,4'-isopropylidene bisphenols, 4,4'-n-butylidene bisphenols, 4,4'-oxy bisphenols, 4,4'-thio bisphenols, 4,4'-sulfinyl bis phenols, 4,4'-sulfonyl bisphenols, and the like; 4,4'-methylene bis(3-t-butyl-5-methylphenol), 4,4'-ethylidene bis(3-t-butyl-5-methyphenol), 4,4'-propylidene bis(3-6-butyl-5-methylphenol, 4,4'-isopropylidene bis(3-t-butyl-5-methylphenol), 4,4'-n-butylidene bis(3-t-butyl-5-methylphenol), 4,4'-oxy bis(3-t-butyl-5-methylphenol), 4,4'-thio bis-(3-t-butyl-5-methylphenol), 4,4'-sulfinyl bis(3-t-butyl-5-methylphenol), 4,4'-sulfonyl bis(3-t-butyl-5-methylphenol), 4,4'-methylene bis(3-t-butyl-5-butylphenol), 4,4'-ethylidene bis(3-t-butyl-5-butylphenol), 4,4'-propylidene bis(3-t-butyl-5-butylphenol), 4,4'-isopropylidene bis(3-t-butyl-5-butylphenol), 4,4'-n-butylidene bis(3-t-butyl-5-butylphenol), 4,4'-oxy bis(3-t-butyl-5-butylphenol), 4,4'-thio bis(3-t-butyl-5-butylphenol), 4,4'-sulfinyl bis(3-t-butyl-5-butylphenol), 4,4'-sulfonyl bis(3-t-butyl-5-butylphenol), 4,4'-methylene bisphenol, 4,4'-ethylidene bis(3-methyl-5-propylphenol), 4,4'-propylidene bis(3-methylphenol), 4,4'-isopropylidene bis(3-methylphenol), 4,4'-n-butylidene bis (3-methylphenol), 4,4'-oxy bis(3-methylphenol), 4,4'-thio bis(3-t-butyl-5-isopropylphenol), 4,4'-sulfinyl bis(3-methyl-5-isopropylphenol), 4,4'-sulfonyl bis(3-methyl-5-isopropylphenol), and the like.

The hydroxyphenylalkyleneyl isocyanurate compounds used in combination with the defined diphosphites of this invention have the formula

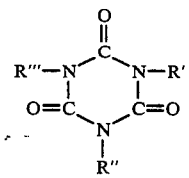

wherein R' is a hydroxyphenylalkyleneyl radical of the formula

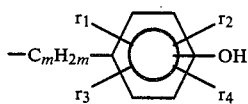

where m is 1 to 4, $r_1$ is an alkyl radical having 1 to 18 carbon atoms and is positioned immediately adjacent to the hydroxy group on the ring; $r_2$, $r_3$, and $r_4$ are hydrogen or an alkyl radical containing 1 to 18 carbon atoms; and R" and R'" are hydrogen, an alkyl radical containing 1 to 18 carbon atoms, or are the same as R'. A more preferred compound is when R" and R'" are equal to R', i.e., all the R groups are hydroxyphenylalkyleneyl radicals, and $r_1$ is a t-alkyl radical containing from 4 to about 12 carbon atoms, $r_2$ is an alkyl radical containing from 1 to about 12 carbon atoms, $r_3$ and $r_4$ are hydrogen, and m is 1.

Even more preferred are the symmetrical tris (3,5-di-tert-alkyl-4-hydroxybenzyl) isocyanurates of the formula

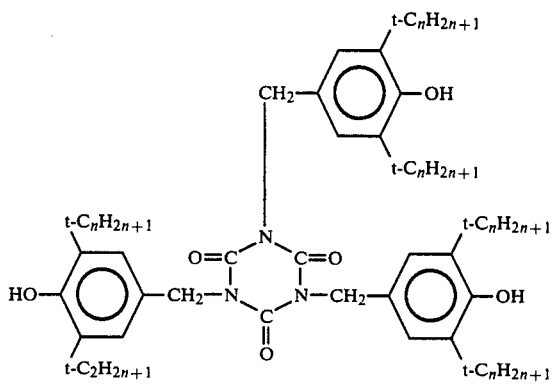

wherein n is 4 to 8.

Examples of the 4-hydroxybenzyl isocyanurate compounds are: tris(3-t-butyl-4-hydroxybenzyl) isocyanurate, tris(3-cetyl-4-hydroxybenzyl) isocyanurate, tris(3,5-dimethyl-4-hydroxybenzyl) isocyanurate, tris (3-methyl-5-isopropyl-4-hydroxybenzyl) isocyanurate, tris-(3,5-di-t-butyl-4-hydroxybenzyl) isocyanurate, tris(3-t-butyl-5-t-amyl-4-hydroxybenzyl) isocyanurate, tris[3,5-di(1-methyl-1-ethylpropyl)-4-hydroxybenzyl] isocyanurate, tris[3,5-di-(1,1,2,2-tetramethylpropyl)-4-hydroxybenzyl] isocyanurate, bis(3,5-dimethyl-4-hydroxybenzyl) isocyanurate, (3-methyl-4-hydroxybenzyl) isocyanurate, (3-t-butyl-4-hydroxybenzyl) isocyanurate and the like. Reference is made to U.S. Pat. No. 3,531,483 which discloses isocyanurate compounds encompassed by this invention. This disclosure of this patent is incorported herein by reference.

The amount of tetrakis(2,6-di-t-butyl-4-substituted phenyl)-4,4'-substitutedbisphenyl diphosphites used may vary from about 0.01 to 10 weigh parts per 100 weight parts of material to be stabilized. About 0.1 to 4.0 parts are normally used for mixtures with the hydroxyphenylalkyleneyl isocyanurate. The hydroxyphenylalkyleneyl isocyanurate compound is used at a level from about 0.01 weight part to about 5 parts by weight, and more preferably at from about 0.05 part to about 3 parts by weight per 100 parts by weight of the organic material. The diphosphite compound is employed at similar levels, i.e., from about 0.01 part to 5 parts and preferably at about 0.05 part to about 3 parts by weight per 100 parts by weight of organic material. Thus the combined weight of the compounds is normally from about 0.02 part to about 10 parts and more preferably from about 0.1 to 6 parts by weight per 100 parts by weight of organic material. The hydroxyphenylalkyleneyl isocyanurate can be used in from about 10:1 to 1:10 weight ratio of isocyanurate compound to diphosphite compound. Excellent results are obtained at about a 3:1 to 1:3 weight ratio. A 1:1 weight ratio of the compounds provides effective stabilization of organic materials.

The following examples represent typical embodiments of the invention, preparation of the novel compounds, stabilizing properties thereof, and the synergistic combination of the defined diphosphites and hydroxyphenylalkyleneyl isocyanurates.

EXAMPLE I

Tetrakis(2,6-di-t-butyl-4-methylphenyl) 4,4'-isopropylidenebisphenyl diphosphite A solution of 0.9 grams of 4,4'-isopropylidenebisphenol (0.004 mol) in 50 ml of dry tetrahydrofuran was added to a reaction vessel equipped with stirring and heating means. While stirring the 4,4'-isopropylidenebisphenol solution under nitrogen, 0.19 gram (0.008 mol) of sodium hydride, as a 50 weight percent dispersion mineral oil was added to the 4,4-isopropylidenebisphenol solution and the resulting mixture was stirred at 55° C. for one hour. The reaction mixture was cooled to room temperature and a solution of bis(2,6-di-t-butyl-4-methylphenyl) phosphorochloridite (4.0 grams, 0.008 mol) in 25 ml of tetrahydrofuran was added to the reaction mixture and the mixture was stirred for three hours. The reaction product was then acidified with 1N HCl and filtered. The filtrate was heated to remove the solvent, and an oily reaction product was obtained. This oil was stirred with 50 ml of acetonitrile for one hour. The resulting white powder was recovered by filtration and dried. The product yield of tetrakis(2,6-di-t-butyl-4-methylphenyl)-4,4'-isopropylidenebisphenyl diphosphite was 3.72 grams. The molecular weight, FD/MS was 1164. NMR data obtained was, (CDCl$_3$): 1.44 (S, 72H), 2.23 (S, 12H), 6.01 (d, J=8.4, 4H), 6.69 (d, J=8.4, 4H), 7.02 (S,8H).

EXAMPLE II

Tetrakis(2,4,6-tris-t-butyl-phenyl) 4,4'-isopropylidenebisphenyl diphosphite

A solution of 1.16 grams of 4,4'-isopropylidenebisphenol (0.005 mol) in 50 ml of dry tetrahydrofuran was added to a reaction vessel equipped with stirring and heating means. While stirring the 4,4'-isopropylidenebisphenol solution under nitrogen, 0.24 gram (0.01 mol) of sodium hydride, as a 50 weight percent dispersion in mineral oil was added to the 4,4-isopropylidenebisphenol solution and the resulting mixture was stirred at 55° C. for one hour. The reaction mixture was cooled to room temperature and a solution of bis(2,4,6-tri-t-butylphenyl) phosphorochloridite (6.0 grams, 0.01 mol) in 25 ml of tetrahydrofuran was added to the reaction mixture and the mixture was stirred for three hours. The reaction product was then acidified with 1N HCl and filtered. The filtrate was heated to remove the solvent, and an oily reaction product was obtained. This oil was stirred with 50 ml of acetonitrile for one hour. The resulting white powder was recovered by filtration and dried. The product yield of tetrakis(2,4,6-tri-t-butylphenyl)-4,4'-isopropylidenebisphenyl diphosphite was 4.87 grams. The molecular weight, FD/MS was 1332.

EXAMPLE III

Tetrakis(2,6-di-t-butyl-4-methylphenyl)4,4'-sulfonylbisphenyl diphosphite

A solution of 0.74 gram of 4,4'-sulfonylbisphenol (0.003 mol) in 50 ml of dry tetrahydrofuran was added to a reaction vessel equipped with stirring and heating means. While stirring the 4,4'-sulfonylbisphenol solution under nitrogen, 0.14 gram (0.006 mol) of sodium hydride, as a 50 weight percent disperson in mineral oil was added to the 4,4-sulfonylbisphenol solution and the resulting mixture was stirred at 55° C. for one hour. The reaction mixture was cooled to room temperature and a solution of bis-(2,6-di-t-butyl-4-methylphenyl) phosphorochloridite (3.0 grams, 0.006 mol) in 25 ml of tetrahydrofuran was added to the reaction mixture and the mixture was stirred for three hours. The reaction product was then acidified with 1N HCl and filtered. The filtrate was heated to remove the solvent, and an oily reaction product was obtained. This oil was stirred with 50 ml of acetonitrile for one hour. The resulting white powder was recovered by filtration and dried. The product yield of tetrakis(2,6-di-t-butyl-4-methylphenyl)4,4'-sulfonylbisphenyl diphosphite was 2.65 grams. The molecular weight, FD/MS was 1186. NMR data obtained was, (CDCl$_3$): 1.41 (S, 72H), 2.22 (S, 12H), 6.25 (d, J=8.4, 4H), 7.00 (S, 8H), 7.49 (d, J=8.4, 4H).

EXAMPLE IV

Tetrakis(2,4,6-tri-t-butylphenyl)4,4'-sulfonylbisphenyl diphosphite

A solution of 1.27 grams of 4,4'-sulfonylbisphenol (0.005 mol) in 50 ml of dry tetrahydrofuran was added to a reaction vessel equipped with stirring and heating means. While stirring the 4,4'-sulfonylbisphenol solution under nitrogen, 0.24 gram (0.01 mol) of sodium hydride, as a 50 weight percent dispersion in mineral oil was added to the 4,4'-sulfonylbisphenol solution and the resulting mixture was stirred at 55° C. for one hour. The reaction mixture was cooled to room temperature and a solution of bis-(2,4,6-tri-t-butylphenyl) phosphorochloridite (6.0 grams, 0.01 mol) in 25 ml of tetrahydrofuran was added to the reaction mixture and the mixture was stirred for three hours. The reaction product was then acidified with 1N HCl and filtered. The filtrate was heated to remove the solvent, and an oily reaction product was obtained. This oil was stirred with 50 ml of acetonitrile for one one hour. The resulting white powder was recovered by filtration and dried. The product yield of tetrakis-(2,4,6-tri-t-butylphenyl)4,4'-sulfonylbisphenyl diphosphite was 6.0 grams. The molecular weight, FD/MS was 1354.

EXAMPLE V

Tetrakis(2,6-di-t-butyl-4-methylphenyl) 4,4'-thiobisphenyl diphosphite

A solution of 0.65 gram of 4,4'-thiobisphenol (0.003 mol) in 50 ml of dry tetrahydrofuran was added to a reaction vessel equipped with stirring and heating means. While stirring the 4,4'-thiobisphenol solution under nitrogen, 0.14 gram (0.006 mol) of sodium hydride, as a 50 weight percent dispersion in mineral oil was added to the 4,4'-thiobisphenol solution and the resulting mixture was stirred at 55° C. for one hour. The reaction mixture was cooled to room temperature and a solution of bis(2,6-di-t-butyl-4-methylphenyl) phosphorochloridite (3.0 grams, 0.006 mol) in 25 ml of tetrahydrofuran was added to the reaction mixture and the mixture was stirred for three hours. The reaction product was then acidified with 1N HCl and filtered. The filtrate was heated to remove the solvent, and an oily reaction product was obtained. This oil was stirred with 50 ml of acetonitrile for one hour. The resulting white powder was recovered by filtration and dried. The product yield of tetrakis(2,6-di-t-butyl-4-methylphenyl) 4,4'-thiobisphenyl diphosphite was 1.19 grams. The molecular weight, FD/MS was 1154. NMR data obtained was, (CDCl$_3$): 1.44 (S, 72H), 2.24 (S, 12H), 6.06 (d, J=8.4, 4H), 6.85 (d, J=8.4, 4H), 7.30 (S, 8H).

EXAMPLE VI

Tetrakis(2,4,6-tri-t-butylphenyl)4,4'-thiobisphenyl diphosphite

A solution of 1.11 grams of 4,4'-thiobisphenol (0.005 mol) in 50 ml of dry tetrahydrofuran was added to a reaction vessel equipped with stirring and heating means. While stirring the 4,4'-thiobisphenol solution under nitrogen, 0.24 gram (0.01 mol) of sodium hydride, as a 50 weight percent dispersion in mineral oil was added to the 4,4-thiobisphenol solution and the resulting mixture was stirred at 55° C. for one hour. The reaction mixture was cooled to room temperature and a solution of bis(2,4,6-tri-t-butylphenyl) phosphorochloridite (6.0 grams, 0.01 mol) in 25 ml of tetrahydrofuran was added to the reaction mixture and the mixture was stirred for three hours. The reaction product was then acidified with 1N HCl and filtered. The filtrate was heated to remove the solvent, and an oily reaction product was obtained. This oil was stirred with 50 ml of acetonitrile for one hour. The resulting white powder was recovered by filtration and dried. The product yield of tetrakis(2,4,6-tri-t-butylphenyl)4,4'thiobisphenyl diphosphite was 5.3 grams. The molecular weight, FD/MS was 1322.

Test samples of the defined diphosphites in polypropylene were prepared by mixing the stabilizer compounds with polypropylene in a Brabender Plasticorder fitted with a Cam-Head (mixing chamber). The polypropylene is first masticated for 1½ minutes at 190° C. Then the stabilizer mixture is added, followed by 3 minutes additional mixing. The mass is removed and pressed into 20 mil thick sheets. From these sheets are cut 1"×1" plaques for oven-aging. Type C (3"×⅜") tensil bars are cut for UV stability tests.

Thermal/oxidative stability (oven-aging) testing consisted of aging the samples in triplicate in an air-circulating oven at 125° C. The time to catastrophic crumbling (failure) of the plaque is measured and reported as days to failure.

Each sample contained 0.1 weight part of the defined diphosphite per 100 weight parts of polypropylene. The following results were obtained:

I. Tetrakis(2,6-di-t-butyl-4-methylphenyl)4,4'-isopropylidenebisphenyl diphosphite, 5⅓ days.
II. Tetrakis(2,4,6-tri-t-butylphenyl)4,4'-isopropylidenebisphyenyl diphosphite, 5⅓ days.
III. Tetrakis(2,6-di-t-butyl-4-methylphenyl)4,4'-sulfonylbisphenyl diphosphite, 4 days.
IV. Tetrakis(2,4,6-tri-t-butylphenyl)4,4'-sulfonylbisphenyl diphosphite, 5 days.
V. Tetrakis(2,6-di-t-butyl-4-methylphenyl)4,4'-thiobisphenyl diphosphite, 6⅔ days.
VI. Tetrakis(2,4,6-tri-t-butylphenyl)thiobisphenyl diphosphite, 11 days.

Samples containing 0.1 weight part of the defined diphosphites were also tested for ultraviolet light stability, i.e., resistance to degradation by UV radiation. The samples were tested in an Atlas Xenon Weatherometer, Model No. 65-WR, equipped with a 6500 watt Xenon burner tube in accordance with ASTM #D2565-79 -A. The black panel temperature was 60° C. The samples were subjected to an 18 minute water cycle every two hours. The time in hours to a 50% loss in tensile strength was determined. For comparison purposes, tris (β-naphthyl phosphite) was tested and found to have lost 50% tensile strength after 160 hours.

I. Tetrakis(2,6-di-t-butyl-4-methylphenyl)4,4'-isopropylidenebisphenyl diphosphite, 390 hours.
II. Tetrakis(2,4,6-tri-t-butylphenyl)4,4'-isopropylidenebisphenyl diphosphite, 350 hours.
III. Tetrakis(2,6-di-t-butyl-4-methylphenyl)4,4'-sulfonylbisphenyl diphosphite, 490 hours.
IV. Tetrakis(2,4,6-tri-t-butylphenyl)4,4'-sulfonylbisphenyl diphosphite, 380 hours.
V. Tetrakis(2,6-di-t-butyl-4-methylphenyl)4,4'-thiobisphenyl diphosphite, 410 hours.
VI. Tetrakis(2,4,6-tri-t-butylphenyl)thiobisphenyl diphosphite, 460 hours.

To demonstrate the unexpected synergistic enhancement of anti-oxidant activity when the diphosphites of this invention are combined with a hydroxyphenylalkyleneyl isocyanurate, test samples of polypropylene with 0.05 weight part each of tris(3,5-di-t-butyl-4-hydroxybenzyl)isocyanurate and the diphosphites listed below were prepared and tested in the air oven until failure. The results obtained were as follows:

I. Tetrakis(2,6-di-t-butyl-4-methylphenyl)4,4'-isopropylidenebisphenyl diphosphite, 47 days.
II. Tetrakis(2,4,6-tri-t-butylphenyl)4,4'-isopropylidenebisphenyl diphosphite, 44⅓ days.
III. Tetrakis(2,6-di-t-butyl-4-methylphenyl)4,4'-sulfonylbisphenyl diphosphite, 46⅓ days.
IV. Tetrakis(2,4,6-tri-t-butylphenyl)4,4'-sulfonylbisphenyl diphosphite, 39 days.
V. Tetrakis(2,6-di-t-butyl-4-methylphenyl)4,4-thiobisphenyl diphosphite, 85⅓ days.
VI. Tetrakis(2,4,6-tri-t-butylphenyl)thiobisphenyl diphosphite, 136⅝ days.

These values are better than those obtained with commercially available phosphite stabilizers in the same compositions. For example, when these oven aging tests are repeated with 0.1 weight part of tris-(2,4-di-t-butylphenyl)phosphite only, a value of 4 days was obtained. When repeated with this phosphite and the hydroxyphenylalkyleneyl isocyanurate, in amounts of 0.05 weight part each, a value of only 35⅝ days was obtained.

Both the tetrakis(2,6-di-t-butyl-4-substituphenyl)4,4'-substitutedbisphenyl diphosphites and combinations with the isocyanurates provide exceptional heat stability to polyolefin polymers. The combination is especially useful for the stabilization of α-monoolefin homopolymers and copolymers, wherein the α-monoolefin contains 2 to about 8 carbon atoms. High and low-density polyethylene, isotactic and atactic polypropylene, polyisobutylene, and poly(4-methyl-1-pentene) have excellent resistance to ultra violet light when stabilized with the combinations of the present invention. Ethylene-propylene (EP) copolymers and ethylene-propylene (EPDM) terpolymers generally containing less than about 10 percent by weight of one or more monomers containing multiple unsaturation provided, for example, by 1,4-hexadiene, dimethyl-1,4,9-decatriene, dicyclopentadiene, vinyl norbornene, ethylidene norbornene and the like also are stabilized using the combination.

Other organic materials which can be stabilized in accordance with the present invention include both natural and synthetic polymers. For example, the stabilizers are useful for the stabilization of cellulosic materials; natural rubber, halogenated rubber, conjugated diene polymers, as, for instance, polybutadiene, copolymers of butadiene with styrene, acrylonitrile, acrylic acid, alkyl acrylates or methacrylates, methyl vinyl ketone, vinyl pyridine, etc.; polyisoprene, polychloroprene, and the like; vinyl polymers such as poly(vinyl chloride), poly(vinylidene chloride), copolymers of vinyl chloride with vinylidene chloride, polyvinyl acetate, copolymers or vinyl halide with butadiene, styrene, vinyl esters, $\alpha,\beta$-unsaturated ketones and aldehydes, and the like; homopolymers and copolymers of acrylic monomers such as acrylic acid, methacrylic acid, methyl acrylate, methyl methacrylate, ethyl acrylte, 3-ethylhexyl acrylate, acrylamide, methacrylamide, N-methylol-acrylamide, haloacrylates, acrylonitrile, methacrylonitrile, haloacrylates, and the like; epihalohydrin polymers; polyether- or polyol-derived polyurethanes; acetal homopolymers and copolymers; polycarbonates; polyesters such as those derived from maleic, fumaric, itaconic, or terephthalic anhydrides; for example, polyethylene terephthalate; polyamides such as those derived from the reaction of hexamethylenediamine with adipic or sebacic acid; epoxy resins such as those obtained from the condensation of epichlorohydrin with bisphenols; ring opened olefin polymers and the like. Polymer blends, that is, physical admixture of two or more polymers may also be stabilized in accordance with the present invention.

In addition to polymeric materials, the present compounds may stabilize a wide variety of other organic materials. Such compounds include: waxes, synthetic and petroleum-derived lubricating oils and greases; animal oils such as, for example, fat, tallow, lard, cod-liver oil, sperm oil; vegetable oils such as castor, linseed, peanut, palm, cotten seed, and the like; fuel oil; diesel oil, gasoline and the like.

The compounds are readily incorporated into materials to be patented by dissolving or dispersing them with the materials, in liquids, dispersions, solutions, and solid forms. If the material is a solid, especially a polymeric solid such as rubber or a plastic, the compounds can be admixed using mixers such as Banburys, extruders, two-roll mills, and the like, following conventional techniques. One way to disperse the compounds in plastic materials is to dissolve or suspend the compounds in a solvent or diluent, mix the mixture with a plastic in powder or solution form, and then evaporate the solvent.

Compositions containing the novel compounds and combination of compounds can also contain other known compounding ingredients such as filters like carbon black, silica, metal carbonates, talc, and the like; pigments and colorants; curative ingredients like sulfur and peroxides, and vulcanization accelerators; fungicides; processing aids, reinforcing agents and standard ingredients known to the art. Other ingredients known in the art as ultra violet light, thermal and/or oxidative stabilizers can also be used in the stabilized compositions.

I claim:

1. Tetrakis(2,6-di-t-butyl-4-substituted phenyl)4,4'-bisphenyl diphosphite reaction products of (1) about 2 mols of 4-substituted-2,6-t-alkylphenyl phosphorochloridite reaction products of $PCl_3$ and hindered alkylphenols having the formula

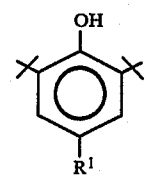

wherein + is t-butyl, $R^1$ is a primary, secondary or tertiary alkyl radical containing 1 to 4 carbon atoms, or $-OR^4$ wherein $R^4$ is an alkyl radical containing 1 to 4 carbon atoms, $-COOR^5$ wherein $R^5$ is an alkyl radical containing 1 to 4 carbon atoms, and $CH_2CH_2COR^6$ wherein $R^6$ is an alkyl radical containing 1 to 4 carbon atoms, with (2) about 1 mol of phenolates of bisphenols of the formula

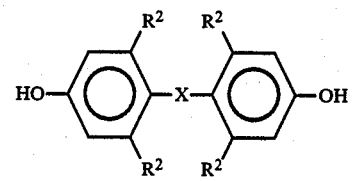

wherein $R^2$ is hydrogen and X is $-S-$, said diphosphites having the formula

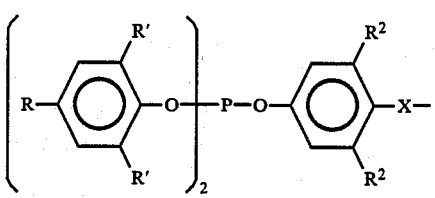

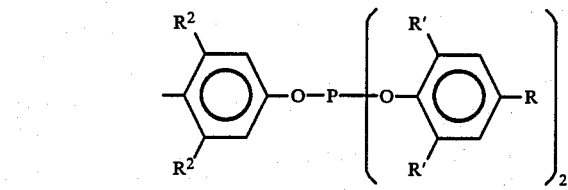

wherein R is an alkyl radical containing 1 to 4 carbon atoms, $-OR^3$ wherein $R^3$ is an alkyl radical containing 1 to 4 carbon atoms, $-COOR^4$ wherein $R^4$ is an alkyl radical containing 1 to 4 carbon atoms and $CH_2CH_2COR^5$ wherein $R^5$ is an alkyl radical containing 1 to 4 carbon atoms; $R^2$ is hydrogen; and X is $-S-$.

2. A disphosphite of claim 1, tetrakis(2,6-di-t-butyl-4-methylphenyl)4,4'-thiobisphenyl diphosphite, wherein the phenolate is sodium 4,4'-thiobisphenyl and the phosphorochloridite is bis(2,6-di-t-butyl-4-methylphenyl)-phosphorochloridite.

3. A diphosphite of claim 1, tetrakis(2,4,6-tri-t-butylphenyl)4,4'-thiobisphenyl diphosphite, wherein the phosphorochloridite is bis(2,4,6-tri-t-butylphenyl)phosphorochloridite and the phenolate is sodium 4,4'-thiobis phenol.

* * * * *